United States Patent
Kawase et al.

(10) Patent No.: US 8,056,393 B2
(45) Date of Patent: Nov. 15, 2011

(54) SIGNAL PROCESSOR FOR GAS SENSOR

(75) Inventors: Tomoo Kawase, Aichi-ken (JP);
Takahito Masuko, Anjo (JP)

(73) Assignee: Denso Corporation, Kariya (JP)

( * ) Notice: Subject to any disclaimer, the term of this patent is extended or adjusted under 35 U.S.C. 154(b) by 143 days.

(21) Appl. No.: 12/536,747

(22) Filed: Aug. 6, 2009

(65) Prior Publication Data
US 2010/0031731 A1 Feb. 11, 2010

(30) Foreign Application Priority Data
Aug. 6, 2008 (JP) ................. 2008-203515

(51) Int. Cl.
*G01N 7/00* (2006.01)
(52) U.S. Cl. .................. 73/23.32; 73/114.72
(58) Field of Classification Search ......... 73/23.31, 73/23.32, 114.71, 114.72
See application file for complete search history.

(56) References Cited

U.S. PATENT DOCUMENTS

| | | | | |
|---|---|---|---|---|
| 4,488,529 A * | 12/1984 | Nishida et al. | ........... | 123/682 |
| 5,289,717 A * | 3/1994 | Ishida | ........... | 73/114.72 |
| 5,615,550 A * | 4/1997 | Ogawa et al. | ........... | 60/276 |
| 6,073,073 A * | 6/2000 | Kitamura et al. | ........... | 701/103 |
| 6,234,012 B1 * | 5/2001 | Lewis et al. | ........... | 73/114.37 |
| 6,453,665 B1 * | 9/2002 | Bower et al. | ........... | 60/285 |
| 6,739,177 B2 * | 5/2004 | Sato et al. | ........... | 73/23.31 |
| 7,606,654 B2 * | 10/2009 | Kawase et al. | ........... | 701/109 |
| 7,614,391 B2 * | 11/2009 | Kawase et al. | ........... | 123/674 |
| 7,776,194 B2 * | 8/2010 | Kawase et al. | ........... | 204/424 |
| 2008/0262704 A1 * | 10/2008 | Kawase et al. | ........... | 701/109 |
| 2009/0064758 A1 * | 3/2009 | Walter et al. | ........... | 73/23.31 |

FOREIGN PATENT DOCUMENTS

JP 2004-150379 5/2004

* cited by examiner

*Primary Examiner* — Freddie Kirkland, III
(74) *Attorney, Agent, or Firm* — Nixon & Vanderhye P.C.

(57) ABSTRACT

The present invention provides, as one aspect, a signal processor for a gas sensor that is disposed in an exhaust passage of an internal combustion engine and senses concentration of a specific component in exhaust gas. The signal processor includes a calculation unit that performs moderation operation at every instant for a sensor output of the gas sensor, an evaluation unit that evaluates a degree of pressure variation impact on the sensor output caused in the exhaust passage, and a change unit that changes a mode of the moderation operation according to a result of the evaluation by the evaluation unit.

13 Claims, 7 Drawing Sheets

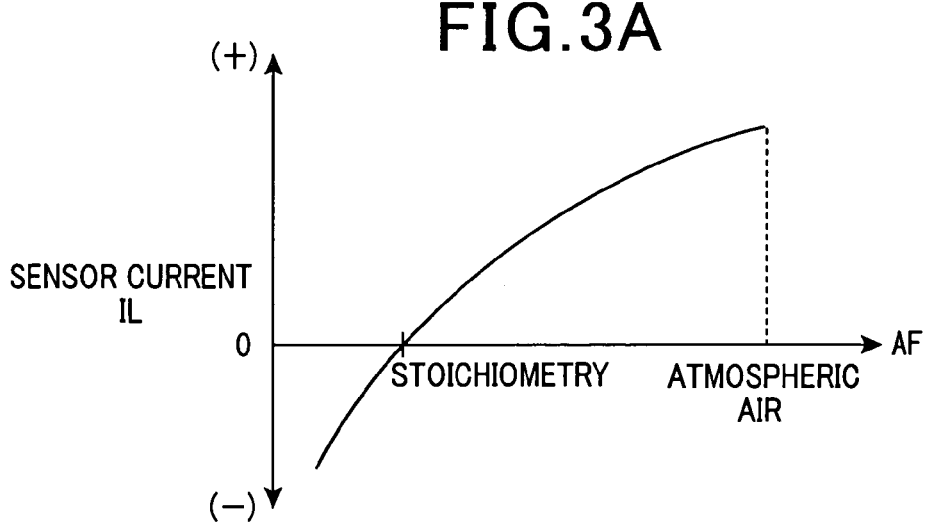
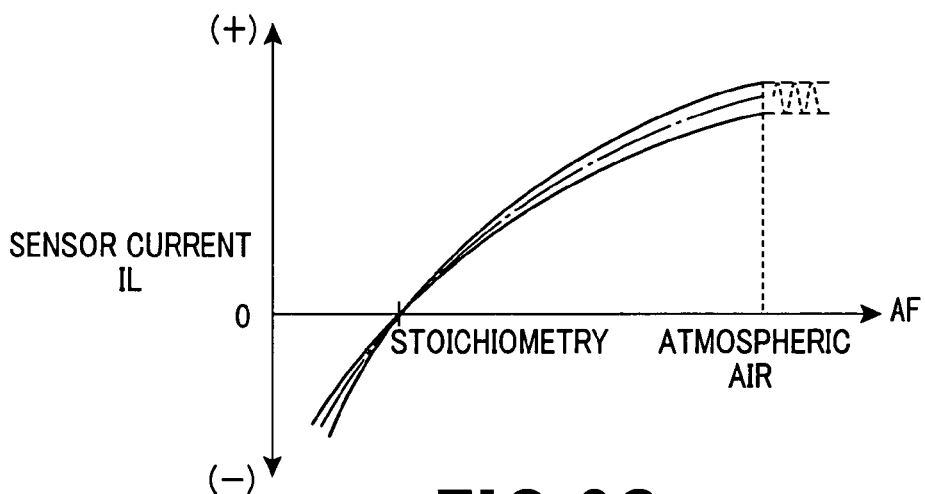
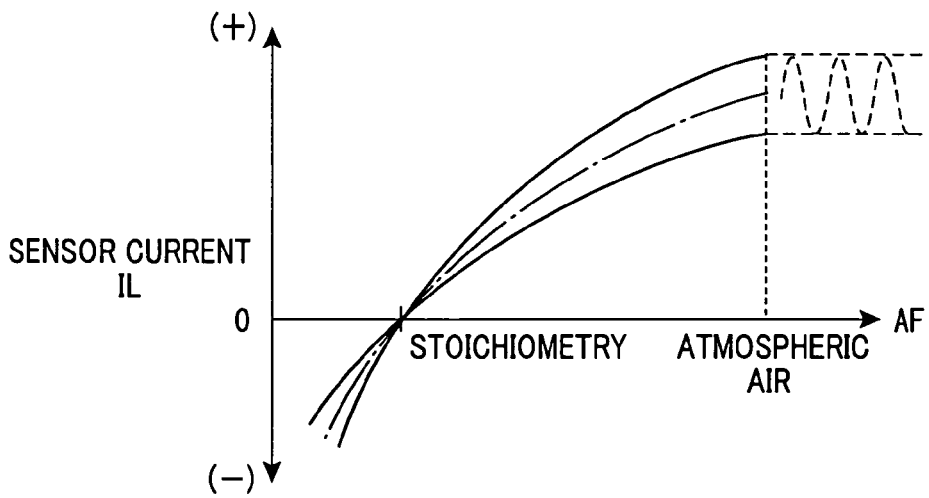

LEAN

IL — MODERATED VALUE

EXHAUST PRESSURE

CLOSE TO STOICHIOMETRY

IL

EXHAUST PRESSURE

RICH

IL — MODERATED VALUE

EXHAUST PRESSURE

SIGNAL PROCESSOR FOR GAS SENSOR

CROSS-REFERENCE TO RELATED APPLICATION

This application is based on and claims the benefit of priority from earlier Japanese Patent Application No. 2008-203515 filed Aug. 6, 2008, the description of which is incorporated herein by reference.

BACKGROUND OF THE INVENTION

1. Technical Field of the Invention

The present invention relates to a signal processor for a gas sensor.

2. Related Art

This type of gas sensor is in practical use as an A/F (air-fuel ratio) sensor, for example, provided at an exhaust passage of an internal combustion engine. The air-fuel ratio of an air-fuel mixture is detected based on the output of the sensor. In an air-fuel ratio control system for an internal combustion engine, air-fuel ratio feedback control is performed in order to have the actual air-fuel ratio that has been detected by the A/F sensor matched with a target air-fuel ratio at every instant.

It is considered that, in the exhaust passage, variation is caused in the exhaust pressure (exhaust pulsation), which causes variation in the output of the A/F sensor induced by the exhaust pulsation. To take measures against the variation in such sensor output induced by exhaust pulsation, Japanese Patent Application Laid-Open Publication No. 2004-150379, for example, suggests a technique with which a moving average process is performed in respect to a plurality of outputs. Performing the moving average process can moderate sensor outputs, whereby an A/F detection value that has been suppressed with the exhaust pulsation can be obtained.

A moving average process performed in respect to a plurality of outputs as mentioned above may reduce the variation in the sensor output, which variation is induced by exhaust pulsation. However, there has been a concern that the moving average process may deteriorate the responsiveness of the sensor output to actual changes of the gas atmosphere (gas concentration change). Specifically, although output occurs in an A/F sensor in response to the actual gas concentration change, the execution of the moving average process by a microcomputer or the like may disable detection of the intrinsic sensor output, or may increase response delay for the intrinsic sensor output.

Recent study, in particular, has put a focus on detecting the air-fuel ratio of each cylinder in a multi-cylinder internal combustion engine and on effecting air-fuel ratio control for each cylinder based on the result of the detection of the air-fuel ratio of the cylinder, in order to further improve the exhaust emissions of the internal combustion engine. Such a cylinder-specific air-fuel ratio is detected based on the output of an A/F sensor provided at an exhaust concentrated portion in the multi-cylinder internal combustion engine. Disadvantageously, however the moving average process performed in respect to the outputs of the sensor as mentioned above may disable highly-responsive detection of the cylinder-specific air-fuel ratio.

SUMMARY OF THE INVENTION

The present invention has a principal object of providing a signal processor for a gas sensor, which is able to achieve a good balance between the reduction of variation in sensor output caused by the pressure variation in a gas atmosphere and the attainment of responsiveness of the sensor output.

In order to achieve the object, the present invention provides, as one aspect, a signal processor for a gas sensor that is disposed in an exhaust passage of an internal combustion engine and senses concentration of a specific component in exhaust gas, comprising: a calculation unit that performs moderation operation at every instant for a sensor output of the gas sensor; an evaluation unit that evaluates a degree of pressure variation impact on the sensor output caused in the exhaust passage; and a change unit that changes a mode of the moderation operation according to a result of the evaluation by the evaluation unit.

BRIEF DESCRIPTION OF THE DRAWINGS

In the accompanying drawings:

FIGS. 3A to 3C are graphs each illustrating a relationship between air-fuel ratio and sensor current;

DETAILED DESCRIPTION OF PREFERRED EMBODIMENTS

Figure 1:
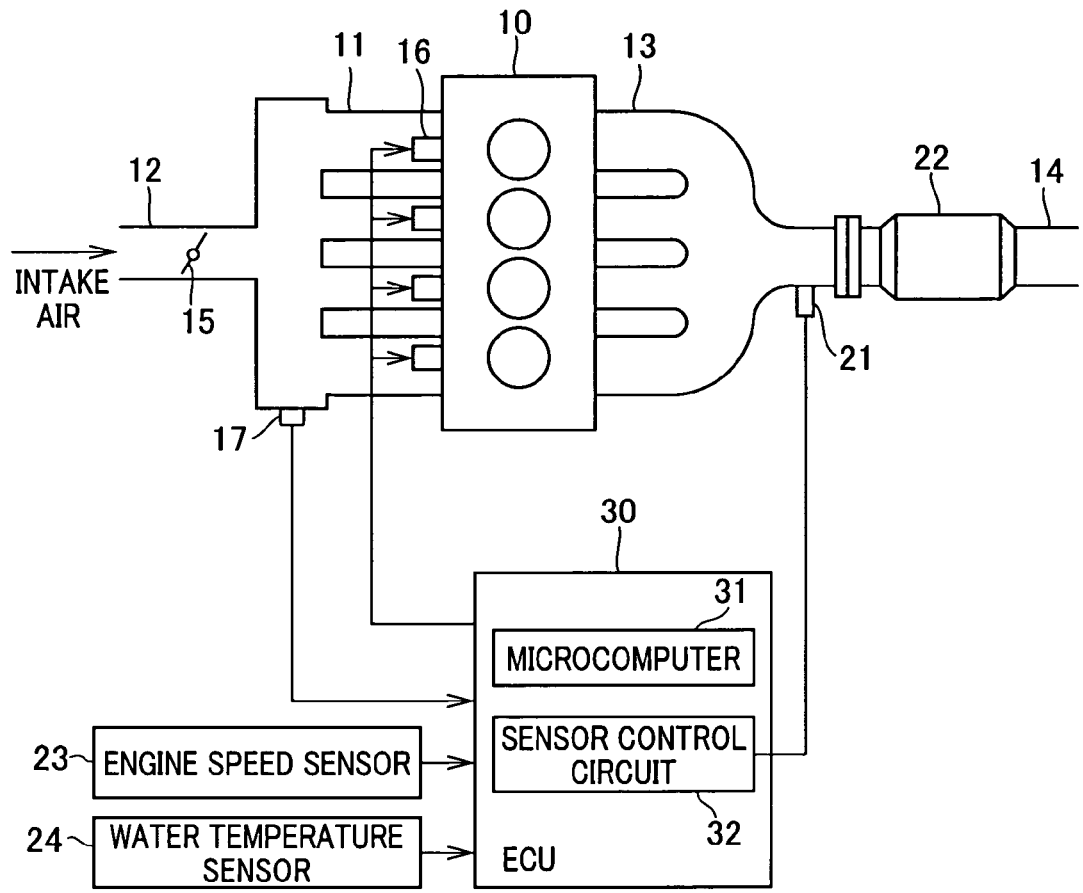
FIG. 1 is a schematic view illustrating a configuration of an engine control system according to an embodiment of the present invention.

With reference to the accompanying drawings, hereinafter is described an embodiment that implements the present invention. The present embodiment is implemented into an engine control system that controls a multi-cylinder spark-ignition type gasoline engine provided in vehicles. The engine control system is adapted to control operating conditions of the gasoline engine by an electronic control unit (ECU). FIG. 1 is a schematic diagram illustrating the engine control system.

In FIG. 1, an engine 10 is a four-cylinder gasoline engine including an intake system and an exhaust system. The intake system is provided with an intake manifold 11 and an intake pipe 12 disposed upstream of the intake manifold 11. The exhaust system is provided with an exhaust manifold 13 and an exhaust pipe 14 disposed downstream of the exhaust manifold 13. The intake system forms an intake passage and the exhaust system forms an exhaust passage. The intake pipe 12 is provided with a throttle valve 15. The engine 10 has an intake port which is provided with fuel injection valves 16 for the respective cylinders. An intake pressure sensor 17 for sensing the pressure in the intake pipe is provided at a converged portion (surge tank) of the intake manifold 11. As an alternative to such a port-injection type engine, an in-cylinder injection type engine may be used as the engine 10.

An A/F sensor 21 is disposed at a converged portion of the exhaust manifold 13, and a catalyst 22, such as a three way catalyst, is disposed downstream of the A/F sensor 21, i.e. at the exhaust pipe 14. The A/F sensor 21 has a sensor element made up of a solid electrolyte, such as zirconia, and is adapted to broadly detect an air fuel ratio (A/F) from a rich region to a lean region by producing current signals (sensor output) in response to rich components (e.g., HC) and lean components ($O_2$) in the exhaust gas. Explanation and illustration is omitted as to other known components, such as intake/exhaust valves and an ignition system, of the engine 10.

In the engine 10, fuel is injected by the fuel injection valves 16 of the respective cylinders in a predetermined combustion order (e.g., #1→#3→#4→#2) to intake air-fuel mixture into the combustion chambers of the respective cylinders with the opening of respective intake valves, not shown. Then, after the air-fuel mixture has been supplied to the individual cylinders, exhaust gas is sequentially discharged from the cylinders to the exhaust manifold 13 with the opening of exhaust valves, not shown.

An ECU 30 is chiefly configured by a known microcomputer 31 including CPU as well as ROM and RAM. The ECU 30 executes various control programs stored in the ROM to perform various controls associated with the operation of the engine 10. Specifically, the ECU 30 is successively inputted with detection signals of the intake pressure sensor 17 and the A/F sensor 21 mentioned above, as well as detection signals from other sensors, such as a speed sensor 23 that senses engine speed and a water temperature sensor 24 that senses engine water temperature. Then, the microcomputer 31 calculates at a predetermined calculation period various parameters, such as an intake pipe pressure PM, an air-fuel ratio AF, an engine speed NE and engine water temperature, that indicate at every instant the operating conditions of the engine, based on the detection signals from these sensors. At the same time, for example, the microcomputer 31 permits the fuel injection valves 16 to control the quantity of fuel injection and permits the ignition system to control the timing of ignition. To specify the fuel injection quantity control, the microcomputer 31 sets a target air-fuel ratio based on an every instant engine operating condition, while performing air-fuel ratio feedback control so that the actual air-fuel ratio calculated based on an output of the A/F sensor 21 coincides with the target air-fuel ratio.

The air-fuel ratio feedback control is explained further as follows. In the present embodiment, a cylinder-specific air-fuel ratio is detected based on an output of the A/F sensor 21, and a cylinder-specific correction value of air-fuel ratio is calculated based on the cylinder-specific air-fuel ratio, for the purpose of eliminating variation in the air-fuel ratio between cylinders. Then, a fuel injection quantity is controlled for each cylinder, based on the cylinder-specific correction value of air-fuel ratio.

The variation in the air-fuel ratio between cylinders is ascribed to the individual differences of the fuel injection valves 16 in the respective cylinders, differences in performance due to aging, or differences in the amount of intake air of the individual cylinders. In recent years, a technique has been in practical use, in which valve-opening operation of the intake valves of the individual cylinders is regulated by the operation of an adjustable valve mechanism, and the air quantity to be taken into the individual cylinders is controlled by the opening/closing of the intake valves. Therefore, the intake air quantity is likely to be differentiated between cylinders, which fact creates a factor of causing variation in the air-fuel ratio between cylinders.

Figure 2:
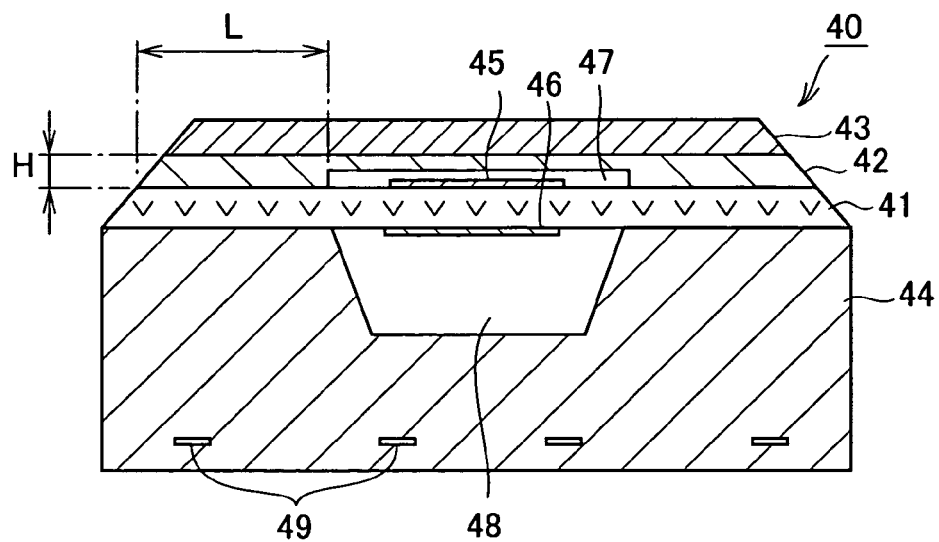
FIG. 2 is a cross-sectional view illustrating a structure of a sensor element.

Referring to FIG. 2, hereinafter is described the configuration of the A/F sensor 21. FIG. 2 is a cross-sectional view illustrating the inner structure of a sensor element 40 having a stacked structure.

The sensor element 40 includes a solid electrolyte layer 41, a diffusion resistance layer 42, a shielding layer 43 and an insulating layer 44, all of which are vertically stacked as viewed in the figure. A protective layer, not shown, is provided around the sensor element 40. The solid electrolyte layer 41 is a rectangular sheet made of partially stabilized zirconia, with a pair of electrodes 45, 46 being vertically disposed sandwiching the solid electrolyte layer 41. The diffusion resistance layer 42 is made up of a porous sheet that introduces exhaust gas to the electrode 45. The shielding layer 43 is made up of a compact layer that suppresses permeation of the exhaust gas. The diffusion resistance layer 42 is provided with an exhaust chamber 47 that surrounds the electrode 45. It should be appreciated that the diffusion resistance layer 42 corresponds to a "gas diffusion introducing portion", and the solid electrolyte layer 41 and the electrodes 45, 46 correspond to a "concentration sensing portion".

The diffusion resistance layer 42 and the shielding layer 43 are each obtained by molding ceramics, such as alumina, spinel or zirconia, using a sheet molding process, for example. Gas permeability is adapted to differ, depending on the average pore size and the void content of the porosity.

The insulating layer 44 is made of high thermal conductivity ceramics, such as alumina, with an atmospheric duct 48 being formed at a portion facing the electrode 46. The insulating layer 44 is also embedded with heaters 49. The heaters 49 are each made up of a linear heater that generates heat with the supply of current from a battery power source. The entire element is heated by the heat generation. In the following description, of the pair of electrodes 45, 46 sandwiching the solid electrolyte layer 41, the electrode 45 on the side of the exhaust chamber 47 is also referred to as a "gas sensing electrode 45", and the electrode 46 on the side of the atmospheric duct 48 is also referred to as a "reference electrode 46".

In the sensor element 40 configured as described above, the exhaust gas around the sensor element (the exhaust gas in the exhaust passage) is introduced from the lateral portions of the diffusion resistance layer 42. The exhaust gas then flows into the exhaust chamber 47 passing through the diffusion resistance layer 42 to reach the gas sensing electrode 45. If the exhaust gas is lean, oxygen in the exhaust gas is dissolved by the gas sensing electrode 45. Then, the resultant exhaust gas is discharged from the reference electrode 46 into the atmospheric duct 48 through the solid electrolyte layer 41. In this case, sensor current (corresponding to positive current) passes in a direction from the reference electrode 46 to the gas sensing electrode 45 in the sensor element 40. On the other hand, if the exhaust gas is rich, oxygen in the atmospheric duct 48 is dissolved by the reference electrode 46. Then, the resultant exhaust gas is discharged from the gas sensing electrode 45 into the exhaust chamber 47 through the solid electrolyte layer 41. In this case, sensor current (corresponding to negative current) passes in a direction from the gas sensing electrode 45 to the reference electrode 46 in the sensor element 40.

Referring again to FIG. 1, the ECU 30 is provided with a sensor control circuit 32 that measures current passing through the sensor element of the A/F sensor 21 (the sensor current passing across the pair of electrodes). The sensor control circuit 32 will now be described briefly. The sensor control circuit 32 includes a current measuring portion that measures sensor current. A sensor current signal resulting from the current measurement at the current measuring portion is amplified with a predetermined amplification factor and outputted the microcomputer 31. The microcomputer 31 calculates the air-fuel ratio AF at every instant based on the sensor current signal (sensor current IL) inputted from the sensor control circuit 32.

FIG. 3A is a graph illustrating a relationship between the air-fuel ratio AF and the sensor current IL. For example, in the state where AF=stoichiometry (14.7), i.e. oxygen concentration=0%, the sensor current IL is "0 mA". When AF=rich, the sensor current IL is negative, and, as the degree of richness becomes higher, the sensor current IL becomes larger on the negative side. Also, when AF=lean, the sensor current IL is positive, and, as the degree of leanness becomes higher, the sensor current IL becomes larger on the positive side.

The sensor control circuit 32 has other functions than the sensor current measuring function described above. In particular, the sensor control circuit 32 has a function of controlling applied voltage to variably control the voltage applied to the sensor in response to sensor current at every instant, a function of detecting impedance of the sensor element, and a function of controlling heaters to control current supplied to the heaters, for keeping the sensor element in an activated state.

In the exhaust passage of the engine 10, pressure variation occurs in synchronization with the combustion period, while the sensor current (sensor output) is varied being induced by the pressure variation. To explain further, combustion occurs in the individual cylinders of the engine 10 in a predetermined order. After the combustion, each exhaust valve is opened, so that the exhaust gas is discharged into the exhaust passage (exhaust manifold 13). At this time, the exhaust pressure rises every time the exhaust valve is opened in each cylinder. When all of the cylinders are concerned, the exhaust pressure varies (i.e. the exhaust pulsation occurs) in synchronization with the combustion period (also referred to as an exhaust period). In this case, when the gas (exhaust gas) is supplied to the exhaust chamber 47 through the diffusion resistance layer 42 in the sensor element 40 of the A/F sensor 21, the molecular weight per unit gas in the exhaust chamber 47 will be varied, being influenced by the pressure of the gas (exhaust pressure). Thus, the sensor current will also be varied induced by the variation in the molecular weight. In this case, as the change in the exhaust pressure becomes larger, variation in the sensor current also becomes larger.

FIGS. 3B and 3C are graphs each illustrating a relationship between the air-fuel ratio AF and the sensor current IL. As shown in the figures, when the exhaust pulsation occurs, the sensor current IL varies on the positive and negative sides in accordance with the exhaust pulsation. The variation in the sensor current IL (amplitude) alters in accordance with the rate of exhaust pressure change, FIGS. 3B and 3C are graphs illustrating variation of the sensor output characteristics in accordance with the rate of exhaust pressure change. In each of the figures, the solid lines indicate the upper limit value and the lower limit value of the sensor current IL. In this case, as the rate of exhaust pressure change becomes larger, variation in the sensor current IL also becomes larger.

In recent years, in order to enhance the output responsiveness of the A/F sensor 21 to the change of air-fuel ratio, study has been conducted of the enhancement of the porosity of the diffusion resistance layer 42 made of a porous material. The enhancement of the porosity is considered to accelerate the tendency that the sensor output is influenced by the exhaust pulsation (sensitivity to pulsation).

To take a measure for the variation of the sensor current IL in response to the exhaust pulsation described above, moderation operation is conducted in the microcomputer 31 every time the sensor current IL is sampled (obtained). The moderation operation corresponds to a smoothing process that smoothes time-series data of the sensor current IL which is sampled at a predetermined period. For example, the moderation operation is executed based on the following Formula (1). In Formula (1), "ILsm" represents a moderating value and "K" represents the moderating rate. A suffix (i) of the moderating value "ILsm" indicates a present value and a suffix (i−1) indicates a previous value.

$$ILsm(i)=ILsm(i-1)\times(K-1)/K+IL\times(1/K) \qquad (1)$$

With the moderation operation being executed for sensor current IL at every instant, the variation in the sensor current IL, which can be caused by the exhaust pulsation, can be removed.

On the other hand, however, the execution of the moderation operation for the censor current may deteriorate the output responsiveness to the actual change of the gas atmosphere. In other words, even when the gas atmosphere in the exhaust passage has actually changed, the change of the gas atmosphere will resultantly be removed from the sensor current after moderation. In particular, in detecting a cylinder-specific air-fuel ratio in order to eliminate variation of the air-fuel ratio between cylinders, it is considered that the execution of the moderation operation for sensor current may be likely to disable detection of the variation between cylinders.

According to the findings of the inventors of the present invention, the impact of exhaust pulsation on the sensor current (sensor output) in the A/F sensor 21 is not constant but changes in large or small scale, depending, for example, on the gas atmosphere and the engine operating conditions. In this regard, the present embodiment evaluates the degree of impact of exhaust pulsation on the sensor current, and changes the mode of moderation operation based on the degree of impact.

Changing the mode of moderation operation includes switching the moderation operation between execution and non-execution and changing the moderating rate of the moderation operation. For example, if the degree of impact of exhaust pulsation on the sensor current is large (if sensor output variation is likely to occur), the moderation operation is executed. Contrarily, if the degree of impact is small (if sensor output variation is unlikely to occur), the moderation operation is not executed. Alternatively, if the degree of impact of exhaust pulsation on the sensor current is small, the moderating rate of the moderation operation is made smaller compared to the case where the degree of impact is larger.

Specifically, the parameters indicating the degree of impact of exhaust pulsation on the sensor current include: (1) the gas atmosphere; (2) the engine speed; and (3) the rate of exhaust pressure change. The present embodiment evaluates the degree of impact of exhaust pulsation on the sensor current IL based on these parameters, and the mode of moderation operation is changed based on the results of the evaluation.

(1) To supplement the gas atmosphere, it has been confirmed that variation is barely caused in the sensor current by the exhaust pulsation if there are almost no lean components ($O_2$) and rich components (e.g., HC) in the exhaust gas, i.e. if the exhaust gas corresponds to a stoichiometric atmosphere (stoichiometry or proximate is to stoichiometry). Contrarily, it has also been confirmed that variation is caused in the sensor current by the exhaust pulsation if the gas atmosphere turns to a lean or rich atmosphere.

Figure 4A:
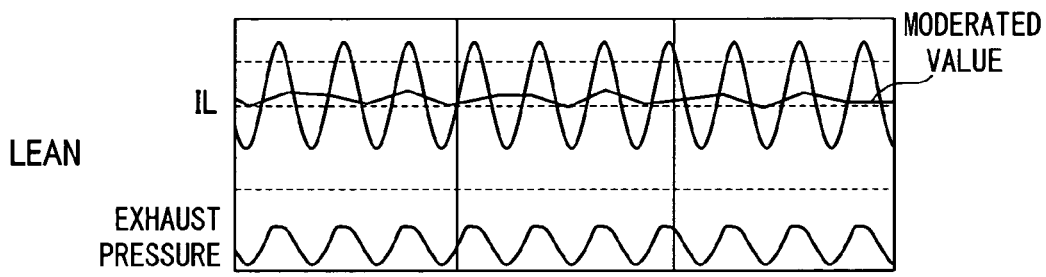
FIG. 4A is a time diagram illustrating the variation in sensor current in a state where the air-fuel ratio is lean.
Figure 4B:
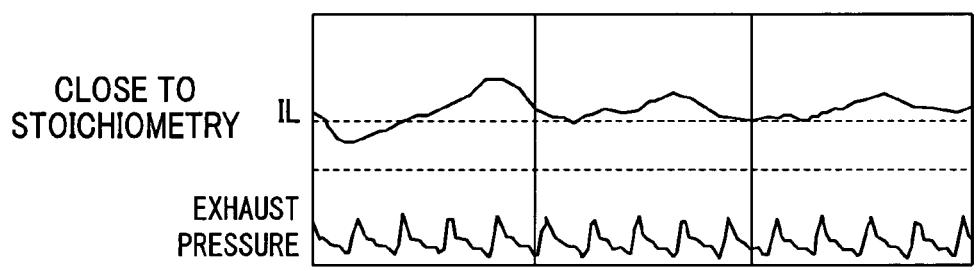
FIG. 4B is a time diagram illustrating the variation in sensor current in a state where the air-fuel ratio is close to stoichiometry.
Figure 4C:
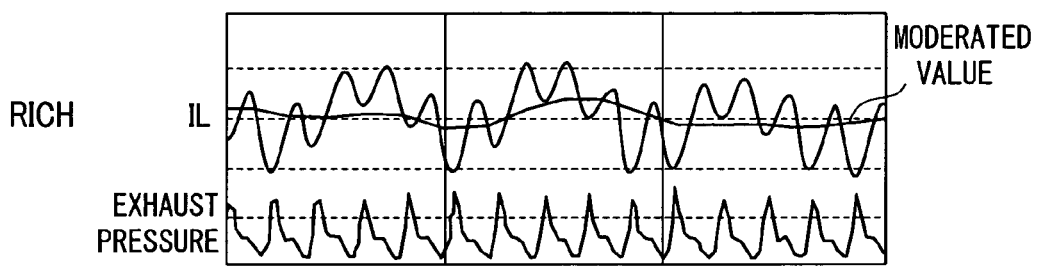
FIG. 4C is a time diagram illustrating the variation in sensor current in a state where the air-fuel ratio is rich.

FIGS. 4A to 4C are graphs illustrating variation of the sensor current when the air-fuel ratio is lean, proximate to stoichiometry, and rich, respectively. In each of FIGS. 4A to 4C, the transition of the sensor current IL is indicated at the upper part, and the transition of the exhaust pressure is indicated at the lower part.

As shown in FIGS. 4A and 4C, when the air-fuel ratio is lean or rich, large variation is caused in the sensor current IL in response to the exhaust pulsation. In other words, the sensor current IL is in a state of suffering from a large degree of impact of exhaust pulsation. It has also been confirmed that the degree of impact of exhaust pulsation becomes larger, as the degree of richness or leanness of the sensor current IL becomes larger, or, as the degree of divergence from the stoichiometric value (0 mA) becomes larger in the sensor current IL. In each of FIGS. 4A and 4C, the current transition indicated by the dash-dot-dot line is the waveform of the sensor current after the moderation operation.

On the other hand, when the air-fuel ratio is proximate to stoichiometry as shown in FIG. 4B, almost no variation can be caused in the sensor current IL in response to the exhaust pulsation. In other words, the sensor current IL is in a state of suffering from a small degree of impact of exhaust pulsation. The reason why variation can be barely caused in the sensor current IL in response to the exhaust pulsation in the stoichiometric atmosphere is that it is considered that there is almost no reaction gas.

In FIG. 4B, the sensor current IL increases at a 720° CA period (corresponding to four periods of exhaust pulsation). This is because air-fuel ratio offset (air-fuel ratio variation between cylinders) due to control error, for example, has been caused in any one of the four is cylinders of the engine 10. One approach for eliminating the air-fuel ratio offset is to carry out the cylinder-specific air-fuel ratio feedback control.

Thus, the degree of impact of exhaust pulsation is evaluated as being small when the sensor current IL equals to the stoichiometric value (substantially 0 mA), and then the moderation operation is ensured not to be performed. Also, the degree of impact of exhaust pulsation is evaluated based on a richness or leanness value of the sensor current IL. As the degree of richness or leanness becomes larger, the moderating rate of the moderation operation is ensured to be larger.

Figure 5:
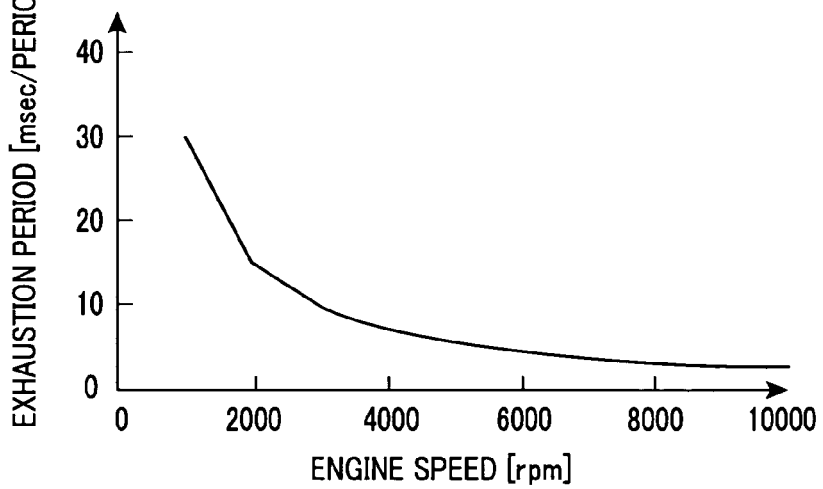
FIG. 5 is a graph illustrating a relationship between engine speed and exhaust period of an engine.

(2) The engine speed is further explained as follows. Comparing the case of low engine speed with the case of high engine speed, variation in the sensor current caused by the exhaust pulsation is smaller in the latter case. FIG. 5 shows a relationship between engine speed and exhaust pulsation period of the engine (hereinafter referred to as "exhaust period"). As can be seen, the higher the engine speed is, the shorter the exhaust period becomes. In a relationship between the exhaust period and a sampling period of the sensor current IL, when the exhaust period becomes substantially the same as the sampling period, or when the exhaust period becomes shorter than the sampling period, the impact of exhaust pulsation will no longer be reflected on the sensor current IL. Taking this into account, the degree of impact of exhaust pulsation on the engine speed is evaluated, and the moderating rate of the moderation operation is adapted to be made larger as the engine speed becomes smaller.

(3) The rate of exhaust pressure change is further explained as follows. Comparing the case of a small rate of exhaust pressure change with the case of a large rate of exhaust pressure change, the variation in the sensor current caused by the exhaust pulsation is larger in the latter case. The rate of exhaust pressure change corresponds to a difference between the minimum value and the maximum value of the exhaust pressure when the exhaust pulsation occurs. In other words, the richness in the gas atmosphere permits the variation of the sensor current IL to be larger on the negative side as the rate of exhaust pressure change becomes larger, and the leanness in the gas atmosphere permits the variation of the sensor current IL to be larger on the positive side as the rate of exhaust pressure change becomes larger (see FIGS. 3B and 3C). Taking this into account, the degree of impact of exhaust pulsation is evaluated based on the rate of exhaust pressure change, and the moderating rate of the moderation operation is adapted to be made larger as the rate of exhaust pressure change becomes larger.

Figure 6:
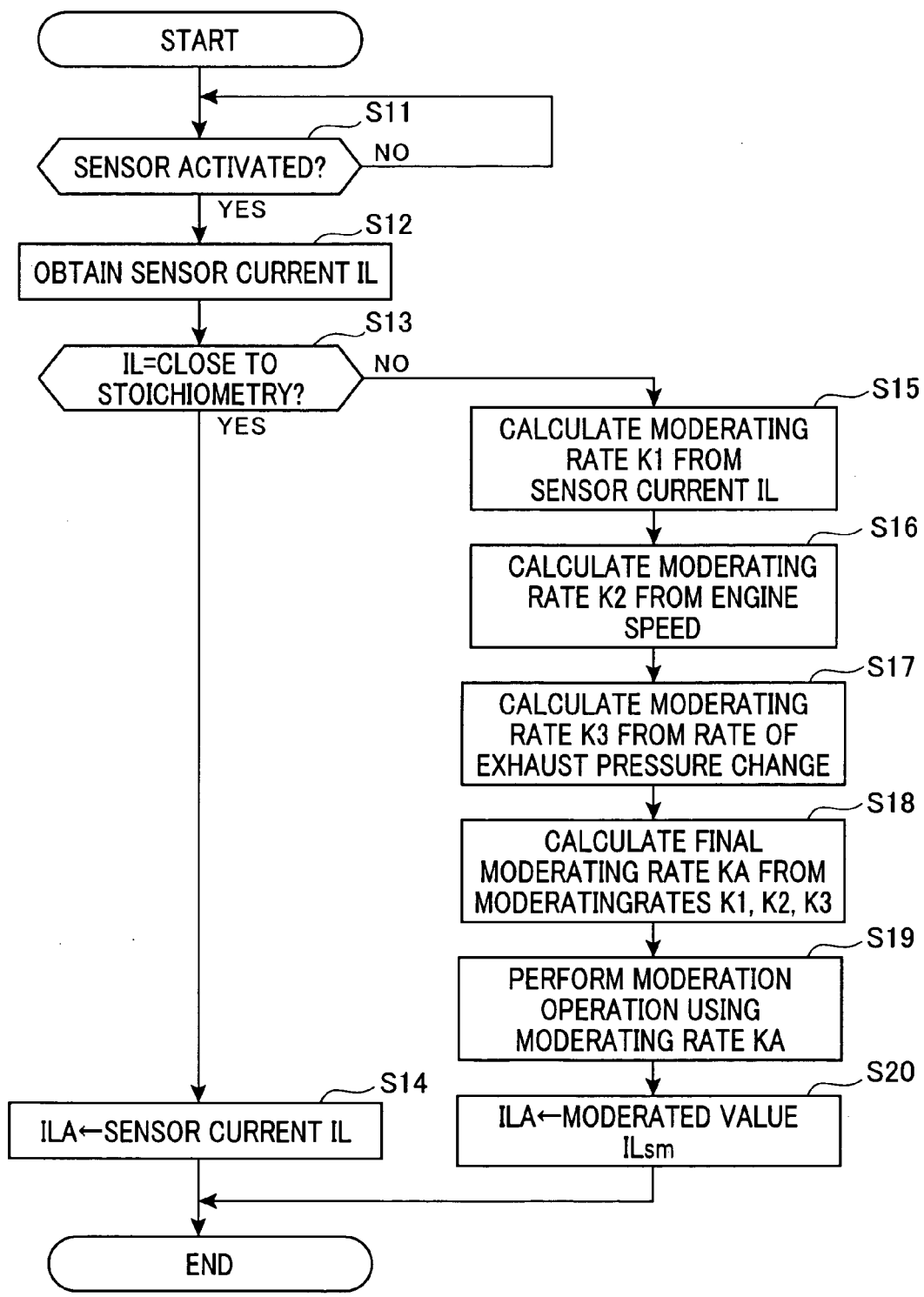
FIG. 6 is a flow diagram illustrating a signal processing procedure for the output signal of an A/F (air-fuel ratio) sensor.

FIG. 6 is a flow diagram illustrating a signal processing procedure for an output signal (sensor current) of the A/F sensor 21. This processing is repeatedly executed at a predetermined time period (e.g. 4 msec) by the microcomputer 31 in the ECU 30.

In FIG. 6, it is determined, in step S11, whether or not activation of the A/F sensor 21 has been completed. If not yet completed, step S11 is repeatedly executed, and if completed, control proceeds to the subsequent step S12. In step S12, a measurement value of the sensor current (sensor current IL) is obtained from the sensor control circuit 32.

After that, in step S13, it is determined whether or not the sensor current IL is proximate to the stoichiometric value (i.e., substantially 0 mA). If YES, control proceeds to step S14, and if NO, control proceeds to step S15.

In step S14, the sensor current IL obtained in step S12 is rendered to be a sensor current ILA to be recognized this time. Specifically, if the sensor current IL is proximate to the stoichiometric value, the sensor current IL is used as it is, without performing the moderation operation for the sensor current IL, to perform the operation based on cylinder-specific air-fuel ratio, for example.

Figure 7A:
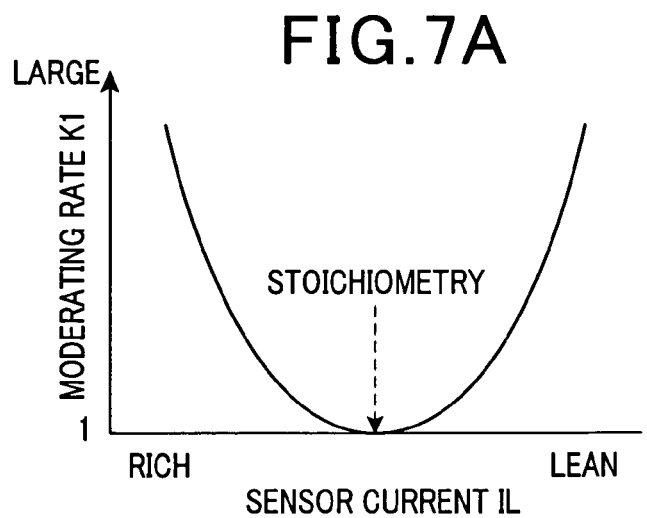
FIG. 7A is a graph illustrating a relationship between sensor current and a moderating rate K1.

In steps S15 to S17, moderating rates K1, K2, K3 are calculated at every instant, based on the gas atmosphere, the engine speed and the rate of exhaust pressure change, respectively. Specifically, in step S15, the moderating rate K1 is calculated based on the sensor current IL at every instant. In this case, the moderating rate K1 is calculated using the relationship shown in FIG. 7A, for example. In FIG. 7A, when the sensor current IL is the stoichiometric value (substantially 0 mA), a relationship K1=1 is established. If the sensor current IL is a rich or lean value, a relationship K1>1 is established. In particular, as the degree of richness becomes larger, or, as the degree of leanness becomes larger, it is ensured that a larger value is established as the moderating rate K1.

Figure 7B:
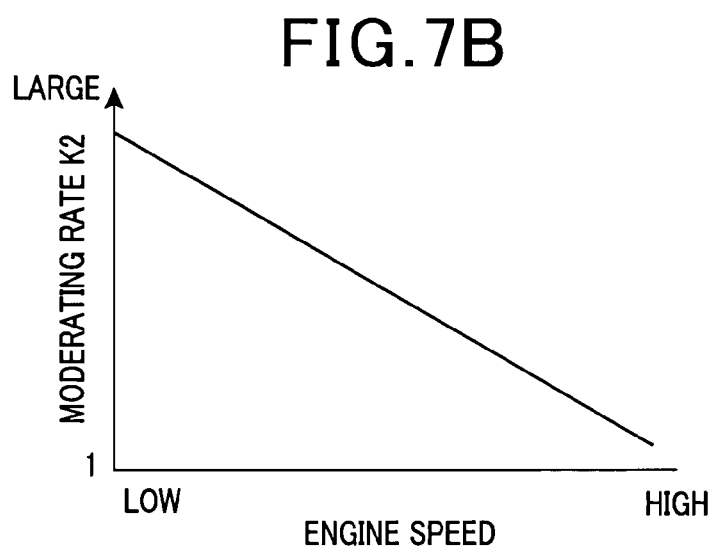
FIG. 7B is a graph illustrating a relationship between engine speed and a moderating rate K2.

In step S16, the moderating rate K2 is calculated based on the engine speed at every instant. In this case, the moderating rate K2 is calculated using the relationship shown in FIG. 7B, for example. In FIG. 7B, as the engine speed becomes higher, a smaller value is ensured to be established as the moderating rate K2.

Figure 7C:
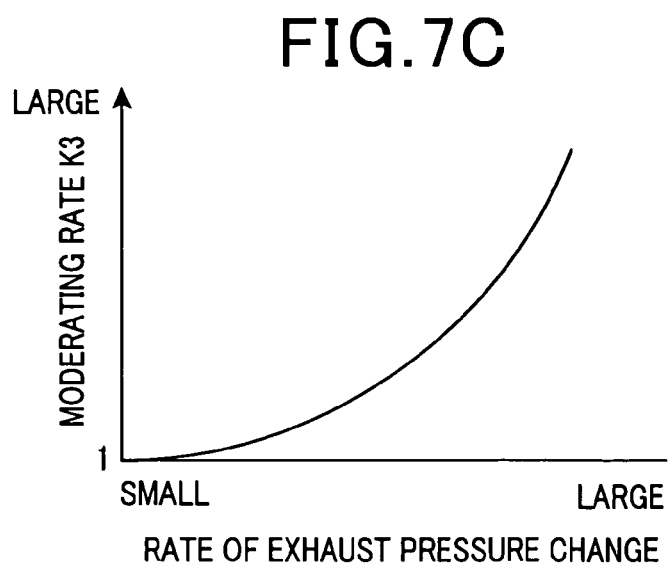
FIG. 7C is a graph illustrating a relationship between a rate of exhaust pressure change and a moderating rate K3.

In step S17, the moderating rate K3 is calculated based on the rate of exhaust pressure change at every instant. In this case, the moderating rate K3 is calculated using the relationship shown in FIG. 7C, for example. In FIG. 7C, as the rate of exhaust pressure change becomes larger, a larger value is ensured to be established as the moderating rate K3.

After that, in step S18, a final moderating rate KA is calculated using the moderating rates K1-K3 calculated above. Specifically, the moderating rates K1-K3 are all multiplied with each other to obtain the final moderating rate KA (KA=K1·K2·K3). Alternatively, the largest value among the moderating rates K1-K3 may be used as the final moderating rate KA (KA=max (K1, K2, K3)).

Then, in step S19, the moderation operation is performed using the final moderating rate KA to calculate a moderating value ILsm of the sensor current. Formula (1) set forth above can be used for the moderation operation.

In step S20, the moderating value ILsm of the sensor current obtained in step S19 is rendered to be the sensor current ILA to be recognized this time. Specifically, if the moderating value ILsm of the sensor current is not proximate to stoichiometry (NO in step S13), the moderation operation is performed for the sensor current IL (step S19), followed by performing the operation for cylinder-specific air-fuel ratio, for example, using the moderating value ILsm after the moderation operation.

According to the present embodiment described above, the following advantages can be obtained.

The above embodiment has been so configured that the degree of impact of exhaust pulsation on the sensor current IL (sensor output) is evaluated, and the mode of the moderation operation is changed based on the results of the evaluation. Thus, the responsiveness of the sensor output can be ensured as needed, unlike the conventional technique of uniformly performing moderation without considering the degree of impact of exhaust pulsation. As a result, a good balance can be ensured between the reduction in the variation of the sensor output caused by the exhaust pulsation and the attainment of the responsiveness of the sensor output.

A certain control system may execute air-fuel ratio feedback control for every cylinder, based on the cylinder-specific air-fuel ratio after detecting the air-fuel ratio of each cylinder. In such a control system, however, performing a moderation operation for the sensor current IL is considered to be disadvantageous, from the viewpoint of detecting a cylinder-specific air-fuel ratio. This is because, regardless of a high-responsive gas concentration (air-fuel ratio) detection of the A/F sensor 21, the highly responsive output is unavoidably moderated.

In this regard, good effect can be exerted if the above-mentioned good balance is ensured between the reduction in the variation of the sensor output caused by the exhaust pulsation, and the attainment of the responsiveness of the sensor output. Specifically, with this good balance being ensured, a sensor output suitable for the gas concentration (particularly, a sensor output corresponding to stoichiometry) can be obtained with high responsiveness, and thus a cylinder-specific air-fuel ratio can be appropriately calculated. In this way, air-fuel ratio feedback control for each cylinder can be executed with high accuracy.

In an attempt to further improve the exhaust emission, it is considered that the need for the cylinder-specific air-fuel ratio feedback control will intensify in the future, but this need will be well satisfied.

As a specific means for changing the mode of moderation operation in the case where the degree of impact of exhaust pulsation is relatively small, the moderating rate for the moderation operation has been ensured to be small compared with the case where the degree of impact is larger than that (steps S15 to S17 of FIG. 6). Also, the execution or non-execution of the moderation operation has been ensured to be switched, depending on the degree of impact of exhaust pulsation (step S13 of FIG. 6). Thus, the intrinsic output that should be caused in response to the gas concentration can be obtained, while reduction can be achieved in the variation of the sensor output.

The sensor current IL, the engine speed and the rate of exhaust pressure change have been used as the parameters for indicating the degree of impact of exhaust pulsation on the sensor current IL. There may be a case where the change, for example, in the engine operating conditions changes these parameters, and where the degree of impact of exhaust pulsation is changed according to the change of the parameters. Even in such a case, an appropriate sensor current IL can is be obtained at every instant.

It is considered that the liability of receiving the impact of exhaust pulsation depends on the structure of the sensor concerned. In other words, the liability of receiving the impact of exhaust pulsation may be associated with the degree of gas permeability in the diffusion resistance layer 42. Specifically, the liability of receiving the impact of exhaust pulsation (gas permeability) is considered to chiefly depend on the porosity of the diffusion resistance layer 42 of the sensor element 40, and also to depend on other factors, such as the cross-sectional area of the diffusion resistance layer 42 (the cross-sectional area perpendicular to the direction in which gas permeates) or the diffusion distance. Let us take as an example the A/F sensor having the diffusion resistance layer 42 whose porosity is of a predetermined level (e.g., 40%) or more. Such a sensor may have good output responsiveness, but, on the other hand, may facilitate gas permeation through the diffusion resistance layer 42, and thus may easily receive the impact of exhaust pulsation.

Let us discuss, here, drawing a border line between an A/F sensor which is likely and unlikely to receive the impact of exhaust pulsation. As mentioned above, the liability of receiving the impact of exhaust pulsation (gas permeability) is considered to depend on the porosity as well as the cross-sectional area and diffusion distance of the diffusion resistance layer 42 of the sensor element 40.

Let us assume, here, three A/F sensors (sensors SN1, SN2 and SN3) each having the diffusion resistance layer 42 with different diffusion distance L, cross-sectional area S (=width D×height H) and porosity α to study whether these A/F sensors are likely or unlikely to receive the impact of exhaust pulsation. It should be appreciated that the basic structure of the sensors SN1-SN3 is identical (see FIG. 2) and that the sensor SN1 corresponds to the A/F sensor 21 of the present embodiment. Specific numerical values associated with these three sensors SN1-SN3 are provided below. [Sensor SN1]

$L=1.1$ mm, $D=1.5$ mm, $H=10.02$ mm, $\alpha=60\%$

[Sensor SN2]

$L=11$ mm, $D=6.35$ mm, $H=0.02$ mm, $\alpha=44\%$

[Sensor SN3]

$L=1.4$ mm, $D=19$ mm, $H=0.24$ mm, $\alpha=15\%$

The impact of exhaust pulsation on the sensor output was studied for the three sensors SN1-SN3 through some experiments. As a result, it was confirmed that sensor output of the sensors SN1 and SN2 was varied by the exhaust pulsation, and, accordingly, these sensors were likely to receive the impact of exhaust pulsation. On the other hand, it was confirmed that the sensor output of the sensor SN3 was not varied by the exhaust pulsation (specifically, variation of the sensor output was very small), and, accordingly, this sensor was unlikely to receive the impact of exhaust pulsation.

Regarding the case where the porosity α is used as an index and the threshold is, say, 30% and where a relationship $\alpha \geq 30\%$ is established, the A/F sensor concerned is to be regarded as a sensor likely to receive the impact of exhaust pulsation. Thus, using the porosity α as an index, a distinction can be made between the A/F sensors likely and unlikely to receive the impact of exhaust pulsation. In other words, if the relationship $\alpha \geqq 30\%$ is satisfied in an A/F sensor, it is advantageous to provide a configuration in which the degree of impact of exhaust pulsation on the sensor current IL (sensor output) is evaluated as described referring to FIG. 6, for example, and the mode of moderation operation is changed based on the results of the evaluation.

Figure 8A:
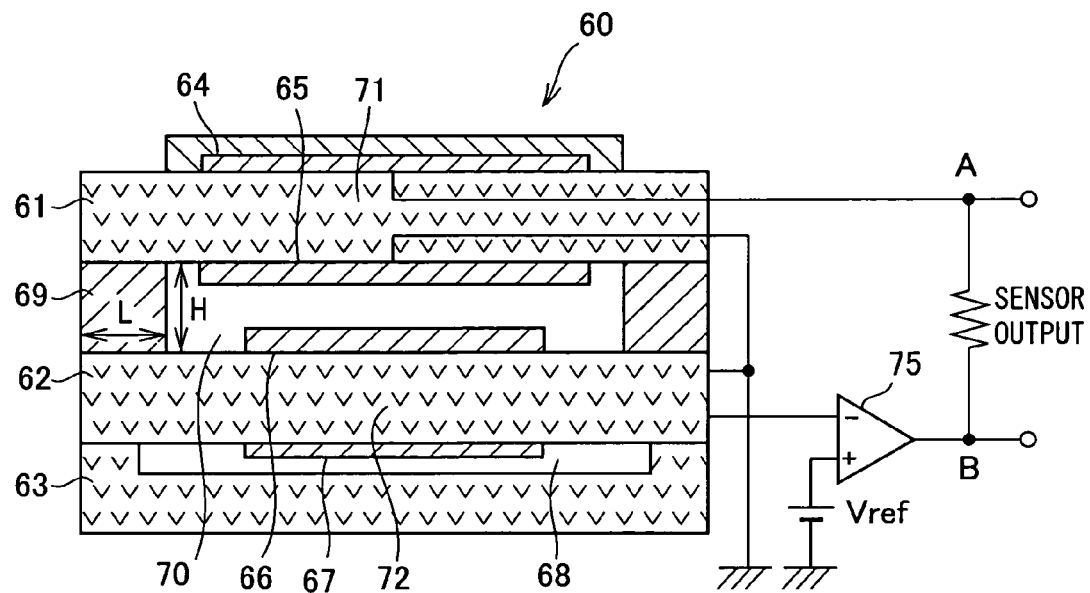
FIGS. 8A and 8B are cross-sectional views each illustrating a structure of another sensor element.
Figure 8B:
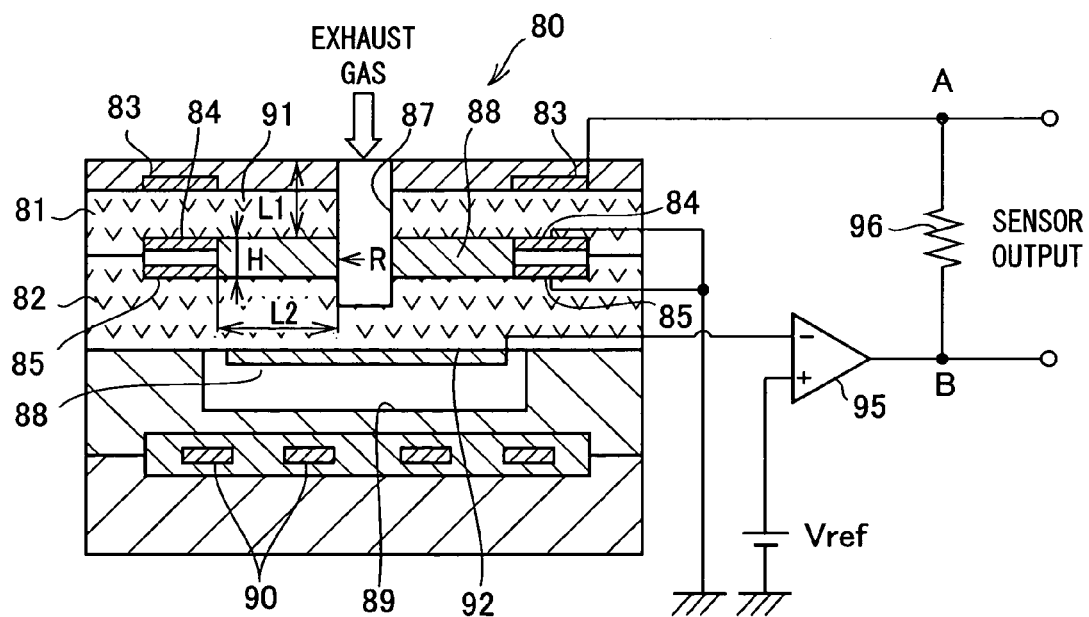

Discussion will now be directed to a sensor element (A/F sensor) having a structure different from the one shown in FIG. 2. For example, a sensor element having a multi-cell structure including a pump cell and an electromotive cell may be used alternative to the sensor element having a one-cell structure. Referring to FIGS. 8A and 8B, hereinafter is briefly described a sensor element having a multi-cell structure. It should be appreciated that a sensor element 60 shown in FIG. 8A has a diffusion-type porous structure similar to the sensor element 40 shown in FIG. 2, and that a sensor element 80 shown in FIG. 8B has a diffusion-type pinhole structure.

The sensor element 60 shown in FIG. 8A has three solid electrolyte layers 61, 62, 63. The solid electrolyte layer 61 has a pair of electrodes 64, 65 facing each other, while the solid electrolyte layer 62 has a pair of electrodes 66, 67 facing each other.

In the sensor element 60, a pump cell 71 is constituted by the solid, electrolyte layer 61 and the electrodes 64, 65, and an oxygen sensing cell 72 is constituted by the solid electrolyte layer 62 and the electrodes 66, 67. The solid electrolyte layer 63 constitutes a wall member that forms an oxygen reference chamber 68. The sensor element 60 is the same as the sensor element 40 described above in that the both have a stacked structure.

Indicated by numeral 69 is a porous diffusion layer and by 70 is a gas sensing chamber (exhaust chamber). The porous diffusion layer 69 corresponds to the "gas diffusion introducing portion". Of the pair of electrodes 64, 65 constituting the pump cell 71, the electrode 65 on the side of the gas sensing chamber 70 corresponds to the "gas sensing electrode (exhaust gas side electrode)", and the electrode 64 on the other side corresponds to the "reference electrode". Generally, the oxygen sensing cell 72 is also referred to as an electromotive cell or an oxygen concentration sensing cell.

The sensor element 60 is provided with a comparator 75 having negative- and positive-side input terminals. The potential of the electrode 67 of the oxygen sensing cell 72 is inputted to the negative-side input terminal of the comparator 75, while comparison voltage Vref is inputted to the positive-side input terminal of the comparator 75. A current sensing resistor 76 is connected between the electrode 64 of the pump cell 71 and the comparator 75. The voltage across both terminals, as indicated by points A and B, of the current sensing resistor 76 is adapted to be taken out as a sensor output. In this case, during a lean period, current flows through the current sensing resistor 76 in a direction of B→A. During a rich period, current flows through the current sensing resistor 76 in a direction of A→B.

The sensor element 80 shown in FIG. 8B has two solid electrolyte layers 81, 82. One solid electrolyte layer 81 has a pair of electrodes 83, 84 facing each other, and the other solid electrolyte layer 82 has a pair of electrodes 85, 86 facing with each other. In the figure, the electrodes 83-85 may each appear to be symmetrically provided at two positions in the horizontal direction. But, the two sets of the electrodes 83-85 provided at the two positions are connected with each other at portions positioned at a front side or rear side with respect to the paper surface, and constitute continuous members.

In the sensor element 80, a pump cell 91 is constituted by the solid electrolyte layer 81 and the electrodes 83, 84, while an oxygen sensing cell 92 is constituted by the solid electrolyte layer 82 and the electrodes 85, 86. The sensor element 80 is the same as the sensor element 40 described above in that both have a stacked structure.

Indicated by numeral 87 is a gas introducing hole (pinhole), by 88 is a disk-shaped porous diffusion layer, by 89 is an atmospheric duct, and by 90 is a heater. The disk-shaped porous diffusion layer 88 is disposed enclosing the gas introducing hole 87. The electrodes 84, 85 are disposed on the outer peripheral side of the diffusion layer 88.

The gas introducing hole 87 and the porous diffusion layer 88 correspond to the "gas diffusion introducing portion". Of the pair of electrodes 83, 84 constituting the pump cell 91, the electrode 84 on the side of the porous diffusion layer 88 corresponds to the "gas sensing electrode (exhaust gas side electrode)" and the electrode 83 on the other side corresponds to the "reference electrode".

The sensor element 80 is provided with a comparator 95 having negative- and positive-side input terminals. The potential of the electrode 86 of the oxygen sensing cell 92 is inputted to the negative-side input terminal of the comparator 95, while comparison voltage Vref is inputted to the positive-side input terminal of the comparator 95. A current sensing resistor 96 is connected between the electrode 83 of the pump cell 91 and the comparator 95. The voltage across both terminals, as indicated by points A and B, of the current sensing resistor 96 is adapted to be taken out as a sensor output.

In the sensor element 80 having the structure described above, the oxygen sensing cell 92 generates binary (0V or 0.9 V) electromotive output according to whether the exhaust gas is lean or rich with respect to the stoichiometry. In a lean period, for example, the electromotive output of the oxygen sensing cell 92 becomes small, while the output of the comparator 95 (the voltage at the point B of FIG. 8B) increases, Accordingly, current flows through the current sensing resistor 96 in a direction of B→A. Contrarily, during a rich period, the electromotive output of the oxygen sensing cell 92 becomes large, while the output of the comparator 95 (the voltage at the point B of FIG. 8B) decreases.

Accordingly, current flows through the current sensing resistor 96 in a direction of A→B. Generally, the oxygen sensing cell 92 is also referred to as an electromotive cell or an oxygen concentration sensing cell.

Let us discuss now the liability of receiving the impact of the exhaust pulsation, in the sensor elements 60 and 80 shown in FIGS. 8A and 8B, respectively. Similar to the sensor element 40 shown in FIG. 2, the sensor element 60 shown in FIG. 8A has a diffusion-type porous structure, Specific numerical values of the porous diffusion layer 69 are as follows:

$$L=0.84 \text{ mm}, D=3.7 \text{ mm}, H=009 \text{ mm}, \alpha=30\%,$$

where L is a diffusion distance, S is a cross-sectional area (=width D×height H), and α is a porosity.

In this case, the A/F sensor having the sensor element 60 can be distinguished as an A/F sensor which is likely to receive the impact of exhaust pulsation. Accordingly, as described above referring to FIG. 6 or the like, it is advantageous for the A/F sensor concerned to have a configuration in which the degree of impact of exhaust pulsation on the sensor current IL (sensor output) is evaluated, and the mode of moderation operation is changed based on the results of the evaluation.

In the sensor element 80 shown in FIG. 5B, the gas diffusion introducing portion is constituted by the gas introducing hole 87 and the porous diffusion layer 88. As to the gas introducing hole 87 in the gas diffusion introducing portion, the radius is represented by R, the distance from the opening of the hole 87 to the porous diffusion layer 88 is represented by L1, and the cross-sectional area is represented by S1 ($=R^2 \cdot \pi$). As to the porous diffusion layer 88 of the gas diffusion introducing portion, the diffusion distance is represented by L2, the cross-sectional area is represented by S2 ($=2 \cdot R \cdot \pi \cdot H$), and the porosity is represented by $\alpha$. Since the gas introducing hole 87 is a pinhole, $\alpha=1$ is established.

In this case, the A/F sensor having the sensor element 80 is distinguished as an A/F sensor which is likely to receive the impact of exhaust pulsation. Accordingly, as described above referring to FIG. 6 or the like, it is advantageous for the A/F sensor concerned to have a configuration in which the degree of impact of exhaust pulsation on the sensor current IL (sensor output) is evaluated, and the mode of moderation operation is changed based on the result of the evaluation.

OTHER EMBODIMENTS

The present invention is not limited to the embodiment described above, but may be implemented as follows.

In the above embodiment, three moderating rates K1-K3 have been calculated based on the gas atmosphere, the engine speed and the rate of exhaust pressure change at every instant, in the signal processing routine shown in FIG. 6, and the moderation operation has been adapted to be conducted using the moderating rates K1-K3. Alternative to this, only any one of the three moderating rates K1-K3 may be ensured to be calculated to conduct the moderation operation.

The above embodiment has been configured not to conduct the calculation of a moderating rate and not to conduct the moderation operation when the sensor current IL is proximate to stoichiometry in the signal processing routine shown in FIG. 6. Alternatively, it may be so configured that the calculation of the moderating rate and the moderation operation may be conducted even when the sensor current IL is proximate to stoichiometry. However, in this case, the moderating rate may be ensured to be approximately "1" when the sensor current IL is proximate to stoichiometry.

Figure 9:
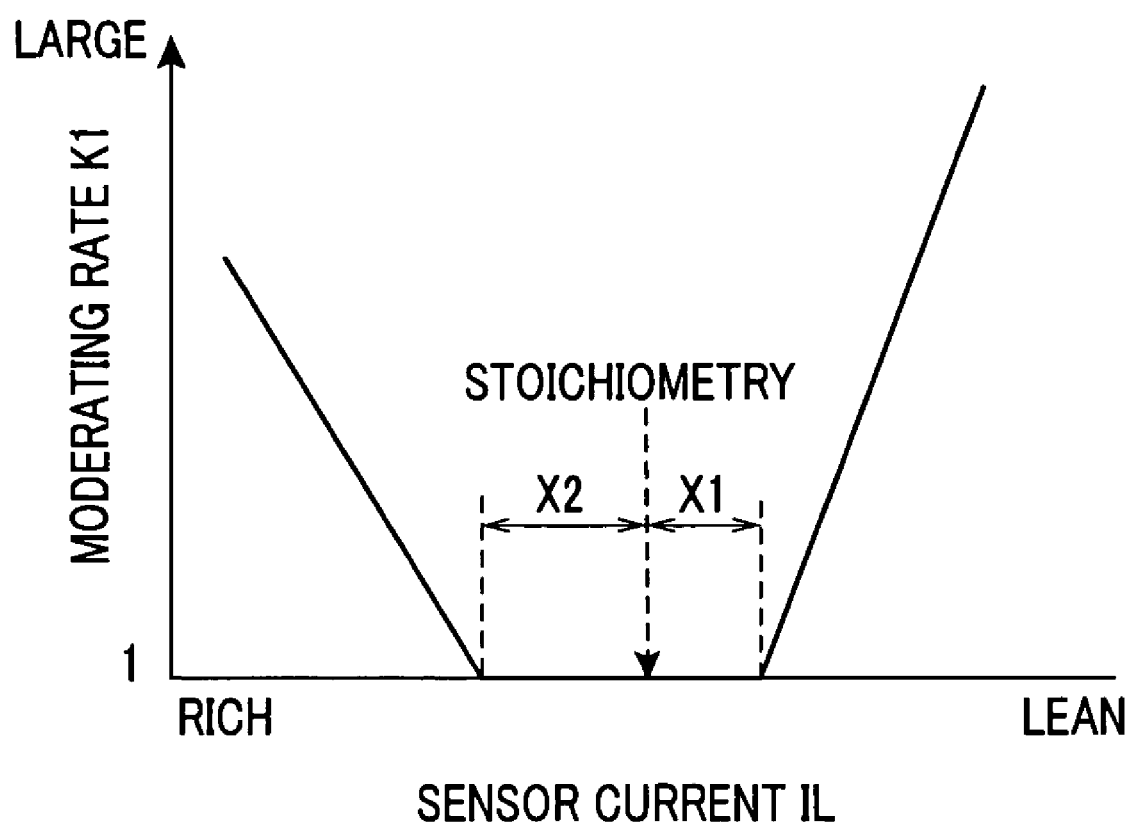
FIG. 9 is a graph illustrating a relationship between sensor current and the moderating rate K1.

In the configuration for calculating the moderating rate K1 based on the sensor current IL at every instant, the moderating rate K1 may be calculated using the relationship shown in FIG. 9. The relationship shown in FIG. 9 is different from the one shown in FIG. 7A in that the rich side and the lean side are asymmetric and that the degree of moderation is tended to be larger on the lean side than on the rich side. This is because the particle size is different between the rich components (e.g., HC) and the lean components ($O_2$) in the exhaust gas and that the latter is considered to easily receive the impact of exhaust pulsation because of the smaller particle size. Specifically:

(1) The increasing rate of the moderating rate K1 for the sensor current IL is made larger on the lean side than on the rich side (lean side slope>rich side slope).

(2) A dead zone X1 (region where K1=1) centering the stoichiometric point on the lean side is made smaller than a dead zone X2 on the rich side.

Either one of the above items (1) and (2) may be applied.

The mode of moderation operation may be configured to be changed (i.e. the moderating rate may be configured to be changed) only when the sensor current IL is either rich or lean.

A moving average process, such as a simple moving average process, a weighted moving average process and an exponentially smoothed moving average process, may be executed as the "moderation operation".

The sampling period of the sensor current IL may be differentiated from the execution period of the moderation operation. For example, the sampling period of the sensor current IL may be 4 msec, while the execution period of the moderation operation may be 10 msec. It may be so configured that the moderation operation is intermittently performed with respect to the sampling of the sensor current IL. Thus, the sampling period of the sensor current IL (IL sampling period) may be differentiated from the moderation execution period so as to become IL sampling period<moderation execution period. Such a differentiation can suppress the processing load from extraordinarily increasing in the case where the engine speed has increased for possible increase of the processing load of the microcomputer.

Specifically, when the engine is in high speed, the period of the exhaust pulsation will become short. In such a case, it is desirable that the sampling period of the sensor current IL is shortened in conformity with the short period of the exhaust pulsation, in order to appropriately detect the air-fuel ratio. However, shortening the execution period of the moderation operation in a manner similar to the sampling period of the sensor current IL will impose a processing load on the microcomputer Taking this into account, the IL sampling period is differentiated from the moderation execution period (IL sampling period <moderation execution period), whereby the microcomputer can be suppressed from being imposed with the extraordinarily increasing processing load.

Further, when the engine is in high speed, various processes associated with engine control may overload the microcomputer (microcomputer in the engine ECU). It is considered that such processes may undesirably increase the processing load of the microcomputer. In such a case as well, it is considered to be advantageous to differentiate the IL sampling period from the moderation execution period (IL sampling period<moderation execution period).

The moderation execution period may be changed based on the engine speed. Specifically, when the engine speed increases, the moderation execution period may be lengthened. Also, the sampling period of the sensor current IL may be an angular period determined based on an engine rotation angle (crank angle).

It may be so configured that the moderating value ILsm of the sensor current is averaged using an update value and past values (values previously obtained, which are "n" in number).

The present invention may be applied not only to A/F sensors or $O_2$ sensors which are able to sense oxygen concentration, but also to gas sensors which are able to detect concentration of other gases, such as Nox and HC. For example, the present invention may be applied to a gas sensor having a plurality of cells formed by solid electrolyte layers. In such a sensor, a first cell (pump cell) may play a role of discharging or charging oxygen from/into the gas to be detected, and a second cell (sensor cell) may play a role of sensing the concentration of a particular component (e.g., NOx or HC) from the gas that has been discharged with oxygen. In other words, the present invention may be applied to an NOx sensor that senses the concentration of NOx in an exhaust gas. Further, the gas sensor may have a plurality of cells including not only the first and second cells mentioned above, but also a third cell (monitor cell or second pump cell) that senses residual oxygen concentration of a gas that has been discharged with oxygen.

Hereinafter, aspects of the above-described embodiments will be summarized.

The signal processor for a gas sensor, which is disposed in an exhaust passage of an internal combustion engine and senses concentration of a specific component in exhaust gas, comprises a calculation unit that performs moderation operation at every instant for a sensor output of the gas sensor, an evaluation unit that evaluates a degree of pressure variation impact on the sensor output caused in the exhaust passage, and a change unit that changes a mode of the moderation operation according to a result of the evaluation by the evaluation unit.

Specifically, it is considered that the sensor output is varied induced by pressure variation which is caused in an exhaust passage of an internal combustion engine in synchronization with the combustion period. In this regard, the moderation operation performed for the sensor output can reduce the variation in the sensor output, which could be caused by the pressure variation in the exhaust passage.

On the other hand, the inventors of the present invention have found that the impact of the pressure variation caused in the exhaust passage (hereinafter just referred to as "pressure variation impact") and incurred on the sensor output is not constant, but changes in large or small scale, depending, for example, on the gas atmosphere or the operating conditions of the internal combustion engine. From this point of view, in the present invention, the degree of pressure variation impact is adapted to be evaluated and the mode of moderation operation is adapted to be changed according to the results of the evaluation. Therefore, responsiveness of the sensor output can be ensured, as needed, in the present invention, unlike the existing technique that uniformly executes moderation operation without considering the degree of pressure variation impact. As a result, the present invention can realize a good balance between the reduction of the sensor output variation that could be caused by the pressure variation in a gas atmosphere and the attainment of the responsiveness of the sensor output.

In the present specification, the "moderation operation" corresponds to the process of smoothing time-series data. Thus, the moderation operation includes moving average processes, such as a simple moving average process, a weighted moving average process and an exponentially smoothed moving average process.

In the signal processor, when the degree of pressure variation impact evaluated by the evaluation unit is relatively small, the change unit may decrease a moderating rate for the moderation operation compared with a case where the degree is relatively large. In this case, an appropriated moderating rate can be set at every instant for a sensor output. When the degree of the pressure variation impact is small, reducing the moderating rate may achieve an intrinsic sensor output that will be produced according to the gas concentration.

In the signal processor, the change unit may switch execution or non-execution of the moderation operation depending on the degree of pressure variation impact evaluated by the evaluation unit. For example, the moderation operation may be ensured to be performed only when the degree of pressure variation impact is large, and no moderation operation may be ensured to be performed when the degree of pressure variation impact is small. Thus, the sensor output variation can be reduced, while the intrinsic sensor output can be obtained, which should be produced according to the gas concentration.

The inventors of the present invention have confirmed that the degree of pressure variation impact on the sensor output can be varied by the following factors.

(1) The gas atmosphere in the exhaust passage
(2) The speed of the internal combustion engine
(3) The rate of pressure change in the exhaust passage As to item (1), it has been confirmed that sensor output will be barely varied by the pressure variation of the exhaust gas, if the exhaust gas contains almost no lean components ($O_2$) and no rich components (e.g., HC) and thus provides a stoichiometric atmosphere (if the exhaust gas is equal to or proximate to stoichiometry). Contrarily, it has also been confirmed that sensor output is varied by the pressure variation in the exhaust gas, if the gas atmosphere turns to a lean or rich atmosphere.

As to item (2), it has been confirmed that, comparing the case where speed of the internal combustion engine is low, with the case where the speed is high, the variation in the sensor output caused by the pressure variation in the exhaust gas is reduced in the latter case.

As to item (3), it has been confirmed that, comparing the case where the rate of pressure change in the exhaust passage is small, with the case where the rate is large, the sensor output variation caused by the pressure variation of the exhaust gas is larger in the latter case.

In light of the above, in the signal processor, the evaluation unit evaluates the degree of pressure variation impact based on a gas atmosphere in the exhaust passage. In this case, the moderation operation is ensured not to be executed, or the moderating rate of the moderation operation is ensured to be reduced, if the gas atmosphere at every instant is unlikely to cause variation in the sensor output. Thus, an appropriate sensor output can be obtained at every instant while considering the variation in the gas atmosphere at every instant in the exhaust passage.

In the signal processor, when the sensor output has an output corresponding to stoichiometry or the vicinity thereof, the evaluation unit evaluates that the degree of pressure variation impact is small, and when the sensor output has an output corresponding to the vicinity of stoichiometry and the evaluation unit evaluates that the degree of pressure variation impact is small, the change unit does not perform the moderation operation. To additionally explain, the moderation operation is adapted to be performed only when the sensor output does not have a value proximate to stoichiometry. Thus, the responsiveness of sensor output can be ensured in the stoichiometric atmosphere (at stoichiometry and its vicinity).

In the signal processor, the evaluation unit uses a degree of divergence from a stoichiometric value of the sensor output as a parameter for indicating the degree of pressure variation impact, and evaluates the degree of pressure variation impact based on the parameter, and the change unit increases a moderating rate of the moderation operation as the degree of divergence becomes larger. Thus, an appropriate sensor output can be obtained at every instant, irrespective of the possible change in the degree of richness or leanness of the gas atmosphere in the exhaust passage. It should be appreciated that the degree of pressure variation impact can be evaluated from at least one of the degree of divergence on the rich side or the degree of divergence on the lean side of the sensor output, with respect to the stoichiometric value.

In the signal processor, the evaluation unit uses at least one of a degree of richness and a degree of leanness of a air-fuel ratio calculated based on the sensor output as a parameter for indicating the degree of pressure variation impact, and evaluates the degree of pressure variation impact based on the parameter, and the change unit increases a moderating rate of the moderation operation as the degree of richness or the degree of leanness becomes larger. Thus, an appropriate sensor output can be obtained at every instant, irrespective of the possible change in the degree of richness or leanness of the gas atmosphere in the exhaust passage.

In the signal processor, the evaluation unit uses an engine speed of the internal combustion engine as a parameter for indicating the degree of pressure variation impact, and evaluates the degree of pressure variation impact based on the parameter, and the change unit increases a moderating rate of the moderation operation as the engine speed becomes smaller. Thus, an appropriate sensor output can be obtained at every instant, irrespective of the possible change in the degree of pressure variation impact, being induced by the change of speed in the internal combustion engine.

In the signal processor, the evaluation unit uses a rate of pressure change in the exhaust passage as a parameter for indicating the degree of pressure variation impact, and evaluates the degree of pressure variation impact based on the parameter, and the change unit increases a moderating rate of the moderation operation as the rate of pressure change becomes larger. Thus, an appropriate sensor output can be obtained at every instant, irrespective of the possible change in the degree of pressure variation impact, being induced by the change of the rate of pressure change in the exhaust passage.

In the signal processor, the gas sensor is an air-fuel ratio sensor provided at an exhaust concentrated portion of a plurality of cylinders of the internal combustion engine, and the signal processor may calculate a cylinder-specific air-fuel ratio based on the sensor output of the gas sensor at every instant. In the case of an air-fuel ratio sensor provided at an exhaust concentrated portion of a plurality of cylinders, an exhaust specific to every cylinder reaches a sensor measurement point in a predetermined combustion order. In such a case, execution of the moderation operation of the sensor output makes it difficult to sense the cylinder-specific air-fuel ratio. In this regard, a cylinder-specific air-fuel ratio can be favorably calculated, by appropriately changing the mode of moderation operation as described above.

In particular, sensor output corresponding to stoichiometry can be obtained in a high-responsive manner for proper calculation of a cylinder-specific air-fuel ratio, in the case where the cylinder-specific air-fuel ratio is calculated based on the output of a gas sensor and where air-fuel ratio feedback control is executed targeting a stoichiometric air-fuel ratio. Thus, air-fuel ratio feedback control can be performed with good accuracy for every cylinder.

The pressure variation impact on a sensor output also depends, in large or small scale, on the structure of the gas sensor. In particular, the inventors of the present invention have confirmed that the pressure variation impact on a sensor output depends on the structure of a gas diffusion introducing portion (such as a so-called diffusion resistance layer) provided at the gas sensor. Specifically, the pressure variation impact relies on how easily gas can pass through the gas diffusion introducing portion of the gas sensor. It is considered that, in a gas sensor having a gas diffusion introducing portion whose porosity is 30% or more, gas can easily pass through the gas diffusion introducing portion, and thus the gas sensor is likely to receive the pressure variation impact.

More specifically, a gas sensor having high responsiveness owing to the porosity of 30% or more in the gas diffusion introducing portion is highly responsive to the change of gas concentration. Therefore, such a gas sensor is likely to cause sensor output variation due to the pressure variation in the exhaust passage. Further, a gas sensor in which the porosity is more than that (e.g., 40% or more, or 50% or more) is more likely to cause sensor output variation due to the pressure variation in the exhaust passage. In such a highly responsive gas sensor, the appropriate change of the mode of moderation operation for sensor output as described above can reduce the sensor output variation in the exhaust passage, while gas concentration detection can be performed taking advantage of the response performance of the gas sensor.

It will be appreciated that the present invention is not limited to the configurations described above, but any and all modifications, variations or equivalents, which may occur to those who are skilled in the art, should be considered to fall within the scope of the present invention.

What is claimed is:

1. A signal processor for a gas sensor that is disposed in an exhaust passage of an internal combustion engine and senses concentration of a specific component in exhaust gas, comprising:
    a calculation unit that performs moderation operation at every instant for a sensor output of the gas sensor, the moderation operation smoothing time-series data of the sensor output;
    an evaluation unit that evaluates a degree of pressure variation impact on the sensor output caused in the exhaust passage; and
    a change unit that changes a mode of the moderation operation according to a result of the evaluation by the evaluation unit.

2. The signal processor according to claim 1, wherein when the degree of pressure variation impact evaluated by the evaluation unit is relatively small, the change unit decreases a moderating rate for the moderation operation compared with a case where the degree is relatively large.

3. The signal processor according to claim 1, wherein the change unit switches execution or non-execution of the moderation operation depending on the degree of pressure variation impact evaluated by the evaluation unit.

4. The signal processor according to claim 1, wherein the evaluation unit evaluates the degree of pressure variation impact based on a gas atmosphere in the exhaust passage.

5. The signal processor according to claim 1, wherein when the sensor output is an output corresponding to stoichiometry or vicinity thereof, the evaluation unit evaluates that the degree of pressure variation impact is small, and
    when the sensor output is an output corresponding to vicinity of stoichiometry and the evaluation unit evaluates that the degree of pressure variation impact is small, the change unit does not perform the moderation operation.

6. The signal processor according to claim 1, wherein the evaluation unit uses a degree of divergence from a stoichiometric value of the sensor output as a parameter for indicating the degree of pressure variation impact, and evaluates the degree of pressure variation impact based on the parameter, and
    the change unit increases a moderating rate of the moderation operation as the degree of divergence becomes larger.

7. The signal processor according to claim 1, wherein the evaluation unit uses at least one of a degree of richness and a degree of leanness of a air-fuel ratio calculated based on the sensor output as a parameter for indicating the degree of pressure variation impact, and evaluates the degree of pressure variation impact based on the parameter, and the change unit increases a moderating rate of the moderation operation as the degree of richness or the degree of leanness becomes larger.

8. The signal processor according to claim 1, wherein the evaluation unit uses an engine speed of the internal combustion engine as a parameter for indicating the degree of pressure variation impact, and evaluates the degree of pressure variation impact based on the parameter, and
    the change unit increases a moderating rate of the moderation operation as the engine speed becomes smaller.

9. The signal processor according to claim 1, wherein the evaluation unit uses a rate of pressure change in the exhaust passage as a parameter for indicating the degree of pressure variation impact, and evaluates the degree of pressure variation impact based on the parameter, and
the change unit increases a moderating rate of the moderation operation as the rate of pressure change becomes larger.

10. The signal processor according to claim 1, wherein the gas sensor is an air-fuel ratio sensor provided at an exhaust concentrated portion of a plurality of cylinders of the internal combustion engine, and
the calculation unit calculates a cylinder-specific air-fuel ratio based on the sensor output of the gas sensor at every instant.

11. The signal processor according to claim 1, wherein the gas sensor comprises a gas diffusion introducing portion provided at a portion where exhaust gas is introduced and a concentration sensing portion which achieves the sensor output by a gas component introduced through the gas diffusion introducing portion, and the gas diffusion introducing portion has a porosity of 30% or more.

12. A signal processor for a gas sensor that is disposed in an exhaust passage of an internal combustion engine and senses concentration of a specific component in exhaust gas, comprising:
a calculation unit that performs moderation operation at every instant for a sensor output of the gas sensor;
an evaluation unit that evaluates a degree of pressure variation impact on the sensor output caused in the exhaust passage; and
a change unit that changes a mode of the moderation operation according to a result of the evaluation by the evaluation unit;
wherein when the sensor output is an output corresponding to stoichiometry or vicinity thereof, the evaluation unit evaluates that the degree of pressure variation impact is small, and
when the sensor output is an output corresponding to vicinity of stoichiometry and the evaluation unit evaluates that the degree of pressure variation impact is small, the change unit does not perform the moderation operation.

13. A signal processor for a gas sensor that is disposed in an exhaust passage of an internal combustion engine and senses concentration of a specific component in exhaust gas, comprising:
a calculation unit that performs moderation operation at every instant for a sensor output of the gas sensor;
an evaluation unit that evaluates a degree of pressure variation impact on the sensor output caused in the exhaust passage; and
a change unit that changes a mode of the moderation operation according to a result of the evaluation by the evaluation unit;
wherein the evaluation unit uses, as a parameter for indicating the degree of pressure variation impact, either:
(i) a degree of divergence from a stoichiometric value of the sensor output,
(ii) at least one of a degree of richness and a degree of leanness of a air-fuel ratio calculated based on the sensor output,
(iii) an engine speed of the internal combustion engine, or
(iv) a rate of pressure change in the exhaust passage;
wherein the evaluation unit evaluates the degree of pressure variation impact based on the parameter; and
wherein the change unit increases a moderating rate of the moderation operation as either:
(i) the degree of divergence from the stoichiometric value becomes larger,
(ii) the degree of richness or the degree of leanness becomes larger,
(iii) the engine speed becomes smaller, or
(iv) the rate of pressure change becomes larger.

* * * * *